United States Patent [19]

Shudo

[11] Patent Number: 5,081,271

[45] Date of Patent: Jan. 14, 1992

[54] BENZOIC ACID DERIVATIVES AND PROCESS FOR PREPARING THE SAME

[76] Inventor: Koichi Shudo, 2-25, 6-102 Higashiyama Meguroku, Tokyo, Japan

[21] Appl. No.: 329,648

[22] Filed: Mar. 28, 1989

[30] Foreign Application Priority Data

Mar. 29, 1988 [JP] Japan .................................. 63-57237

[51] Int. Cl.$^5$ .......................... C07F 7/30; A61K 31/28
[52] U.S. Cl. ...................................... 556/106; 556/87; 556/105; 556/107
[58] Field of Search ................. 556/106, 87, 105, 107; 514/492

[56] References Cited

U.S. PATENT DOCUMENTS

| | | | |
|---|---|---|---|
| 4,271,084 | 6/1981 | Shikawa et al. | 556/87 X |
| 4,361,579 | 11/1982 | Munakata et al. | 514/492 X |
| 4,501,702 | 2/1985 | Butten et al. | 556/87 X |
| 4,579,961 | 4/1986 | Kakimoto | 514/492 X |
| 4,748,187 | 5/1988 | Kakimoto et al. | 514/492 |
| 4,772,628 | 9/1988 | Kakimoto et al. | 556/87 X |
| 4,808,631 | 2/1989 | Klaus | 514/492 X |
| 4,889,715 | 12/1989 | Sawai et al. | 514/492 X |
| 4,898,882 | 2/1990 | Nagahama et al. | 514/492 |

Primary Examiner—Paul F. Shaver
Attorney, Agent, or Firm—Gordon W. Kueschen

[57] ABSTRACT

Benzoic acid derivatives represented by the formula (I):

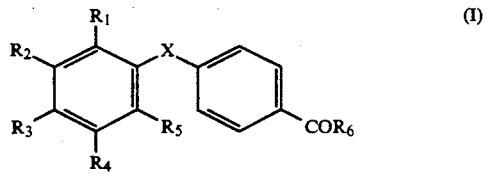

wherein $R_1$ represents hydrogen or lower-alkyl, $R_2$ and $R_4$ represent hydrogen, trimethylsilyl, or trimethylgermyl, $R_3$ represents hydrogen, lower-alkyl, trimethylsilyl, or trimethylgermyl, $R_5$ represents hydrogen, lower-alkyl, acetyl, or hydroxy, at least one of $R_2$ and $R_3$ being trimethylsilyl or trimethylgermyl, and $R_6$ means hydroxy, lower-alkoxy, or a group of the formula —$NR_7R_8$, wherein $R_7$ and $R_8$ mean hydrogen or lower-alkyl, and X represents a group of the formula —COHN—, —NHCO—, —COO—, —OCO—, —COCH=CH—, —COCH=C(OH)—, or —CH=CH—, which exhibit excellent effect as differentiation-inducing agents for neoplastic cells, especially leukemia cells, or a therapeutic agent for psoriasis or immune and inflammatory diseases, and a process for the preparation thereof, are disclosed.

7 Claims, No Drawings

BENZOIC ACID DERIVATIVES AND PROCESS FOR PREPARING THE SAME

BACKGROUND OF THE INVENTION

1. Field of the Invention

The present invention relates to novel benzoic acid derivatives represented by the general formula (I), which have great potential as useful medicaments, and a process for preparing the same.

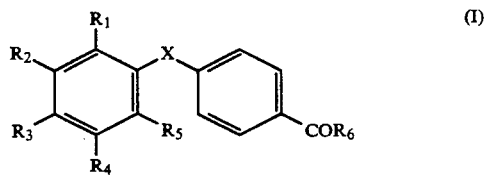
(I)

The variables in the formula are described in detail in the following.

2. Description of the Prior Art

In Japan Kokai 61-22046, 61-22047 and 61-76440, it was already shown that benzoic acid derivatives represented by the general formula (II):

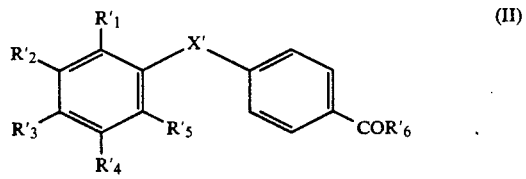
(II)

wherein $R'_1$, $R'_2$, $R'_3$, $R'_4$ and $R'_5$ are the same or different, and each represents hydrogen or middle or lower-alkyl, with the proviso that all can not be hydrogen simultaneously, and wherein two neighboring substituents may be combined with each other to form a cycloalkyl ring having 5 to 6 carbon atoms, $R'_6$ represents hydroxyl, lower-alkoxyl, or lower-alkylamino of the formula —$NR'_7R'_8$, wherein $R'_7$ and $R'_8$ each represents hydrogen or lower-alkyl, and $X'$ represents a group of the formula:

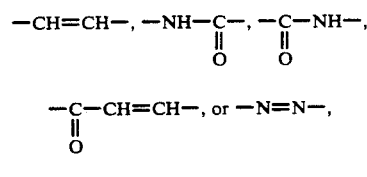

are capable of inducing the differentiation of malignant cells, especially leukemia cells, to morphologically and functionally mature cells which cannot proliferate further, and are accordingly pharmacologically valuable and useful for treatment of malignant proliferous or immune diseases such as cancer, rheumatism, or psoriasis, and in Japan Kokai 62-215581, there are also shown related compounds. The literature also shows the activity and measurement of the activity of those compounds by the differentiation of human acute promyelocytic leukemia cells (HL-60).

Such a compound, wherein $R'_2$, $R'_3$ and $R'_4$ each is a middle alkyl group, especially wherein one alkyl substituent is isopropyl or butyl, and wherein two alkyl substituents $R'_2$ and $R'_3$ are combined into a ring having 5 to 6 carbon atom, is especially effective. On the other hand such a compound, wherein both of $R'_3$ and $R'_4$ are hydrogen, does not exhibit the desired activity. Such a compound, wherein $R'_7$ and $R'_8$ are hydrogen or methyl, and wherein $R'_6$ is hydroxyl or methoxy, is especially effective. The subject of the present invention consists in diminishing the undesirable side-effects which the above-identified compounds are known to possess and providing additional new compounds having the same therapeutic potential.

3. Summary of the invention

It has now been found that benzoic acid derivatives represented by the formula (I):

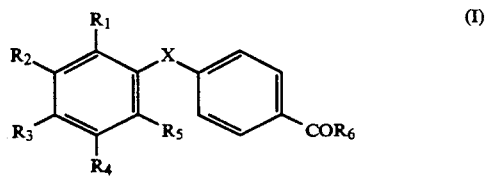
(I)

wherein $R_1$ represents hydrogen or lower-alkyl, $R_2$ and $R_4$ represent hydrogen, trimethylsilyl, or trimethylgermyl, $R_3$ represents hydrogen, lower-alkyl, trimethylsilyl, or trimethylgermyl, $R_5$ represents hydrogen, lower-alkyl, acetyl, or hydroxy, at least one of $R_2$ and $R_3$ being trimethylsilyl or trimethylgermyl, and $R_6$ means hydroxy, lower-alkoxy, or a group of the formula —$NR_7R_8$, wherein $R_7$ and $R_8$ mean hydrogen or lower-alkyl, and X represents a group of the formula —CONH—, —NHCO—, —COO—, —OCO—, —COCH=CH—, —COCH=C(OH)—, or —CH=CH—, exhibit excellent effect as differentiation-inducing agents for neoplastic cells, especially leukemia cells. Further, according to the present invention, there is also provided a process for preparation of the novel benzoic acid derivatives represented by the formula (I).

DETAILED DESCRIPTION OF THE INVENTION

By the term "lower" in formula (I) is meant a straight or branched carbon chain having 1-4 carbon atoms. Therefore, the lower-alkyl moiety of the lower-alkyl group encompassed by $R_1$, $R_3$, $R_5$, $R_7$ and $R_8$ is representatively methyl, ethyl, n-propyl, isopropyl, n-butyl, isobutyl, sec-butyl, and tert-butyl. The lower-alkoxy moiety of the lower-alkoxy group encompassed by $R_6$ is representatively methoxy, ethoxy, n-propoxy, isopropoxy, n-butoxy, etc.

The compounds represented by formula (I) form salts with bases. This invention includes the pharmaceutically-acceptable salts of the compounds of formula (I) and examples of these salts are salts with alkali metals such as sodium, potassium, etc., or alkaline earth metals such as calcium, etc.; salts with ammonia; and salts with organic bases such as methylamine, ethylamine, trimethylamine, triethylamine, pyridine, picoline, arginine, lysine, etc.

The novel benzoic acid derivatives represented by the formula (I) can be prepared by the following methods:

(a) a compound represented by the formula (I), wherein X represents a group of the formula —CONH—, is prepared by condensation of a functional derivatives such as the acid halide or ester, derived from a benzoic acid derivative represented by the formula (III):

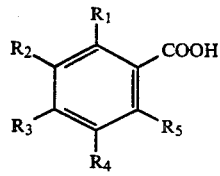

wherein $R_1$, $R_2$, $R_3$, $R_4$ and $R_5$ have the meanings described above, with a p-aminobenzoic acid or its derivative, or (b) a compound represented by the formula (I), wherein X represents a group of the formula —NHCO—, is prepared by condensation of an aniline derivative represented by the formula (IV):

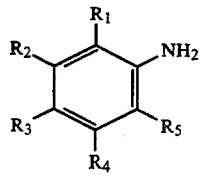

wherein $R_1$, $R_2$, $R_3$, $R_4$ and $R_5$ have the meanings described above, with a functional derivative, such as the acid halide or ester, of terephthalic acid, or (c) a compound represented by the formula (I), wherein X represents a group of the formula —COO—, is prepared by condensation of a functional derivative, such as the acid halide or ester, derived from a benzoic acid derivative represented by the formula (III), with a p-hydroxybenzoic acid or its derivative, or (d) a compound represented by the formula (I), wherein X represents a group of the formula —OCO—, is prepared by condensation of a phenol derivative represented by the formula (V):

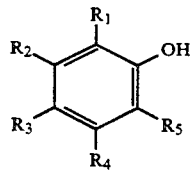

wherein $R_1$, $R_2$, $R_3$, $R_4$ and $R_5$ have the meanings described above, with a functional derivative, such as the acid halide or ester, of terephthalic acid, or (e) a compound represented by the formula (I), wherein X represents a group of the formula —COCH=CH—, is prepared by condensation of an acetophenone derivative represented by the formula (VI):

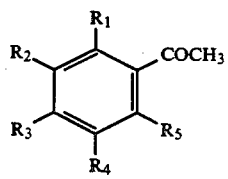

wherein $R_1$, $R_2$, $R_3$, $R_4$ and $R_5$ have the meanings described above, with a terephthalaldehydic acid or its derivative in the presence of a base, or (f) a compound represented by the formula (I), wherein X represents a group of the formula —COCH=C(OH)— and $R_5$ represents hydroxy, is prepared by condensation of an o-hydroxyacetophenone derivative represented by the formula (VII):

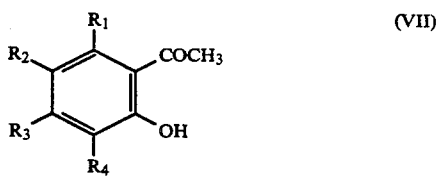

wherein $R_1$, $R_2$, $R_3$ and $R_4$ have the meanings described above, with a terephthalic acid or its derivative to give an ester represented by the formula (VIII):

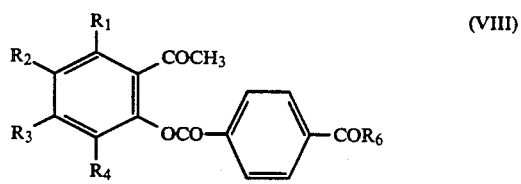

wherein $R_1$, $R_2$, $R_3$, $R_4$ and $R_6$ have the meanings described above, which is followed by rearrangement in the presence of an alkali catalyst, or (g) a compound represented by the formula (I), wherein X represents a group of the formula —CH=CH—, is prepared by condensation of a benzylphosphonium salt represented by the formula (IX):

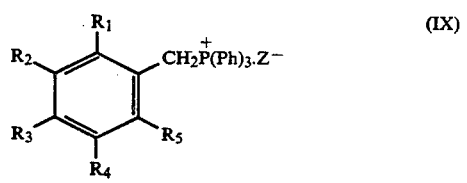

wherein $R_1$, $R_2$, $R_3$, $R_4$ and $R_5$ each have the meanings described above, and Z means halogen, with a terephthalaldehydic acid or its derivative in the presence of a base and, if necessary or desirable, the thus-obtained compound is hydrolyzed using an alkali catalyst.

The compounds having a trimethylsilyl or trimethylgermyl group, which are starting materials, can be prepared in the following manner. One way is using the Grignard reaction with a bromobenzene derivative and trimethylsilyl chloride or trimethylgermyl chloride, as shown in the following scheme:

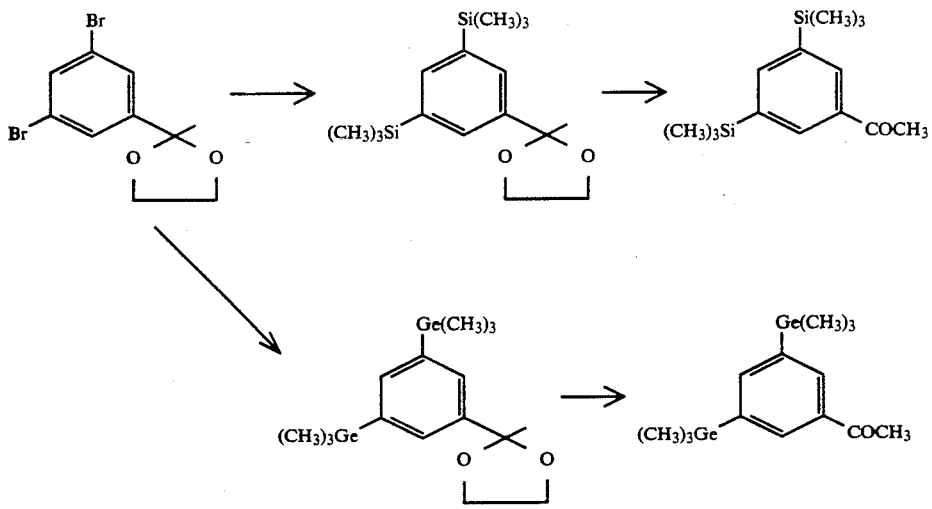

Another way is using an aromatic substitution reaction, which utilizes the de-trimethylsilyl (or germyl) action of poly-trimethylsilyl (or germyl) benzene, as shown in the following scheme:

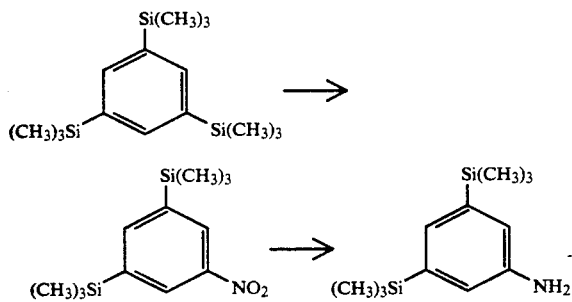

Typical examples of benzoic acid derivatives embraced by the present invention are illustrated below.

4-(3-trimethylsilylphenylcarbamoyl)benzoic acid
4-[3,5-bis(trimethylsilyl)phenylcarbamoyl]benzoic acid
4-(3-trimethylgermylphenylcarbamoyl)benzoic acid
4-[3,5-bis(trimethylgermyl)phenylcarbamoyl]benzoic acid
4-(3-trimethylsilylphenylcarboxamido)benzoic acid
4-[3,5-bis(trimethylsilyl)phenylcarboxamido]benzoic acid
4-[3,5-bis(trimethylgermyl)phenylcarboxamido]benzoic acid
methyl 4-(3-trimethylsilylphenylcarboxy)benzoate
methyl 4-[3,5-bis(trimethylsilyl)phenylcarboxy]benzoate
methyl 4-(3-trimethylgermylphenylcarboxy)benzoate
methyl 4-[3,5-bis(trimethylgermyl)phenylcarboxy]benzoate
4-[3-(3-trimethylsilylphenyl)-3-oxo-1-propenyl]benzoic acid
4-[3-[3,5-bis(trimethylsilyl)phenyl]-3-oxo-1-propenyl]benzoic acid
4-[3-(3-trimethylgermylphenyl)-3-oxo-1-propenyl]benzoic acid
4-[3-[3,5-bis(trimethylgermyl)phenyl]-3-oxo-1-propenyl]benzoic acid
4-[1-hydroxy-3-(2-hydroxy-4-trimethylsilylphenyl)-3-oxo-1-propenyl]benzoic acid
4-[1-hydroxy-3-(2-hydroxy-5-trimethylsilylphenyl)-3-oxo-1-propenyl]benzoic acid
4-[1-hydroxy-3-(2-hydroxy-4-trimethylgermylphenyl)-3-oxo-1-propenyl]benzoic acid
4-[1-hydroxy-3-(2-hydroxy-5-trimethylgermylphenyl)-3-oxo-1-propenyl]benzoic acid
4-[(3-trimethylsilylphenyl)ethenyl]benzoic acid
4-[[3,5-bis(trimethylsilyl)phenyl]ethenyl]benzoic acid
4-[(3-trimethylgermylphenyl)ethenyl]benzoic acid, and
4-[[3,5-bis(trimethylgermyl)phenyl]ethenyl]benzoic acid The compounds represented by formula (I) are all capable of inducing the differentiation of malignant cells, especially leukemia cells, morphologically and functionally, and can therefore be used in the treatment of tumors and cancers, leukemia, T cell malignant diseases, proliferous immune malignant dermatological diseases such as psoriasis, and immune diseases and used for the immunosuppressant in the transplantation of organs. For the therapy of cancer such as T cell lymphoma, acute promyelocytic leukemia, neuroblastoma, and carcinoma, the compounds of this invention can be used systemically, for example by injection or oral administration, in an amount of less than 5 mg/Kg/day, preferably 0.001-1 mg/Kg/day and, for therapy of dermatological diseases such as psoriasis and other dermatological diseases, topically for example as ointments containing the compound itself or a mixture with other medicaments such as a corticosteroid, anthraline, and UV therapeutica, in an amount of 0.1-10 mg of the active compound per gram of ointment.

The test of the activities of the compounds of this invention has been conducted by measuring the concentration required for inducing the differentiation of human acute promyelocytic leukemia cells (HL 60), according to the methods described in detail hereinafter.

Experimental

The compounds of this invention are tested according to established test procedure which shows the differentiation of malignant cells, whereby the differentiation of human acute promyelocytic leukemia cells (HL-60) and their conversion to granulocytes (myelocytes) is assayed by an observation of the morphological changes of nuclei and by the measurement of the degree of reduction of nitro-blue tetrazolium (NBT) which is induced by a test compound (Proc. Natl. Acad. Sci. USA 77, 2936 2940 (1980) with the Title: Induction of differentiation of the human promyelocytic leukemia cell line (HL-60) by retinoic acid). The HL-60 cells are cultured in plastic flasks in RPMI 1640 medium supplemented with 5% heat-inactivated fetal calf serum and antibiotics (penicillin G and streptomycin). The cells ($3 \times 10^4$/ml) are cultured with a compound of the present invention for 4 days. The cells are fixed and stained with Wright-Giemsa to examine the morphological changes of the nuclei.

The cells treated with the compounds of the present invention are differentiated to mature granulocytes (myelocytes, metamyelocytes and neutrophiles), just as the cells treated with retinoic acid. The biochemical activity of cells treated with the compound is measured as follows:

The cells after 5 days incubation are centrifuged and diluted with RPMI 1640 medium, supplemented with 5% fetal calf serum, to provide a definite number of the cells. To the diluted cell suspension are then added 200 ng/ml of 12-o-tetradodecanoylphorbol-13-acetate (TPA) and the resulting culture medium is then incubated for 20 minutes at 37 °C. in the presence of 0.1% of NBT. Thus, the mature differentiated cells containing blue-black formazan are counted by microscope, so that the ratio of the cells having the ability to reduce NBT, to total cells, can be calculated.

The cells treated with a compound of this invention show an NBT reduction activity which corresponds to the important biochemical activity of differentiated cells.

The results of the tests according to the above-mentioned method are summarized in Table 1.

As a positive control for comparison, the known compounds represented by the formula (II) and trans retinoic acid were used.

TABLE 1

| No. | Test Compound | $ED_{50}$ (M)* |
|---|---|---|
| | Present compound | |
| 1. | (structure: $(CH_3)_3Si$-phenyl-NH-C(=O)-phenyl-COOH) | $8 \times 10^{-8}$ |
| 2. | (structure: $(CH_3)_3Si$-phenyl-($Si(CH_3)_3$)-NH-C(=O)-phenyl-COOH) | $2 \times 10^{-8}$ |
| 3. | (structure: $(CH_3)_3Ge$-phenyl-NH-C(=O)-phenyl-COOH) | $3 \times 10^{-8}$ |
| 4. | (structure: $Ge(CH_3)_3$, $(CH_3)_3Ge$-phenyl-C(=O)-CH=CH-phenyl-COOH) | $4 \times 10^{-10}$ |
| 5. | (structure: $Si(CH_3)_3$, $(CH_3)_3Si$-phenyl-C(=O)-CH=CH-phenyl-COOH) | $2 \times 10^{-10}$ |

TABLE 1-continued

| No. | Test Compound | $ED_{50}$ (M)* |
|---|---|---|
| 6. | (structure: $(CH_3)_3Si$-phenyl-CH=CH-phenyl-COOH) | $6 \times 10^{-8}$ |
| | Reference compound | |
| 7. | (structure: tert-Bu-phenyl-C(=O)-CH=CH-phenyl-COOH) | $1 \times 10^{-7}$ |
| 8. | (structure: tert-Bu-phenyl-NH-C(=O)-phenyl-COOH) | $1 \times 10^{-6}$ |
| 9. | (structure: tert-Bu, tert-Bu-phenyl-C(=O)-CH=CH-phenyl-COOH) | $4 \times 10^{-10}$ |
| 10. | retinoic acid | $2 \times 10^{-9}$ |

*$ED_{50}$: Effective doses which cause differentiation of 50% of the cultured cells, M(mol/l).

The results shown in Table 1 indicate that the activity of the compounds of this invention is equal to or greater than that of known compounds of the formula (II) and retinoic acid. Thus, these compounds are very useful in the determination of promyelocytic leukemia and the diseases which is accompanied by hyperkeratinization or inflammation, such as psoriasis, which enables the selection of a proper therapeutical method of approach.

The following References and Examples are given by way of illustration only and are not to be construed as limitations of this invention.

REFERENCE 1 p-Trimethylgermylacetophenone a) 2-(4-Trimethylgermylphenyl)-2-methyl-1,3-dioxolane To a mixture of 108 mg (4.44 mmol) of magnesium and 766 mg (5.00 mmol) of trimethylgermyl chloride was added a solution of 972 mg (4.00 mmol) of 2-(4-bromophenyl)-2-methyl-1,3-dioxolane in 12 ml of dry tetrahydrofuran (THF) at 40 °C. with stirring. The mixture was refluxed for 1.5 hours and stirred at room temperature overnight. An insoluble substance was filtered off and washed with ether. The filtrate and washings were mixed and evaporated. The residue was purified by column chromatography on silica gel [eluent: petroleum ether-methylene chloride (2:1-1:2)] and recrystallized from petroleum ether to give 524 mg of white prisms, m.p.63.5°-65° C.

$^1$H-NMR spectrum $\delta$(CDCl$_3$)ppm: 0.38 (9H,s), 1.66 (3H,s), 3.74-3.83 (2H,m), 4.00-4.08 (2H,m), 7.46 (4H,s).

b) p-Trimethylgermylacetophenone

A solution of 420 mg (1.5 mmol) of 2-(4-trimethylgermylphenyl)-2-methyl-1,3-dioxolane and 56 mg (0.19 mmol) of pyridinium p-toluenesulfonate (PPTS) in 1.35 g (62.5 mmol) of water and 10 ml of acetone was refluxed for 2 hours and stirred at room temperature for 1.5 days. The reaction mixture was extracted with petroleum ether. The extract was washed successively with 2N hydrochloric acid, water and sat.aq.NaHCO$_3$, dried and evaporated.

The residue was purified by column chromatography on silica gel [eluent: methylene chloride-n-hexane (2:3)] to give 344 mg of colorless liquid.

$^1$H-NMR spectrum δ(CDCl$_3$)ppm: 0.41 (9H,s), 2.60 (3H,s), 7.58 (2H,d,J=8.3 Hz), 7.91 (2H,d,J=8.3 Hz).

REFERENCE 2 m-Trimethylsilylaniline a) 1-Nitro-3-trimethylsilylbenzene

To a solution of 1.50 g (6.75 mmol) of m-bis(trimethylsilyl)benzene in 4.0 ml of acetic anhydride was added dropwise a solution of 1.6 ml (35.6 mmol) of 94% nitric acid in 5 ml of acetic anhydride at 130° C. with stirring. The mixture was stirred for 30 minutes. The reaction mixture was poured into a mixture of ice and 2% potassium carbonate solution and methylene chloride and separated. The aqueaus layer was extracted with methylene chloride. The organic layer was washed successively with water and 2% potassium hydroxide solution, dried and evaporated. The residue was purified by column chromatogaphy on silica gel [eluent: methylene chloride-cyclohexane (1:3–1:5)] to give 475 mg of pale yellow liquid.

$^1$H-NMR spectrum δ(CDCl$_3$)ppm: 0.35 (9H,s), 7.50 (1H,t,J=8 Hz), 7.81 (1H,d,J=8 Hz), 8.15 (1H,d,J=8 Hz), 8.32 (1H,s).

b) m-Trimethylsilylaniline m-Nitrotrimethylsilylbenzene (200 mg) was catalytically hydrogenated over Pd-C in 7.5 ml of benzene at atmospheric pressure for 40 minutes. The catalyst was filtered off and washed with benzene and dry MeOH, successively. The filtrate and washings were mixed and evaporated. The residue was purified by column chromatography on silica gel [eluent: methylene chloride] to give 169 mg of pale brown liquid.

$^1$H-NMR spectrum δ(CDCl$_3$)ppm: 0.26 (9H,s), 3.61 (2H,s), 6.6–7.0 (3H,m), 7.16 (1H,t,J=8 Hz).

EXAMPLE 1

4-(3-Trimethylsilylphenylcarbamoyl)benzoic Acid a) Methyl 4-(3-Trimethylsilylphenylcarbamoyl)benzoate To a solution of 135 mg (0.817 mmol) of m-trimethylsilylaniline in 8 ml of dry benzene were added 1.0 ml of dry pyridine and 179 mg (0.900 mmol) of methyl p-chloroformylbenzoate, successively. The mixture was stirred at room temperature for 20 hours. To the reaction mixture was added water and the aqueous solution was extracted with AcOEt. The extract was washed successively with water, sat.eq.NaHCO$_3$ and sat.aq.-NaCl, dried and evaporated to give 272 mg of white powder, which was purified by column chlomatography on silica gel (eluent: methylene chloride) to give 266 mg of white powder (yield: 99%). Recrystallization of the powder from a mixture of methylene chloride, n-hexane and chloroform gave 120 mg of white needles, m.p.125–126° C. (yield 45%).

MS spectrum m/z: 327(M$^+$), 312(M$^+$ –15)

$^1$H-NMR spectrum δ(CDCl )ppm: 0.28 (9H,s), 3.96 (3H,s), 7.3–7.8 (5H,m), 7.98 (2H,d,J=8 Hz), 8.13 (2H,d,J=8 Hz).

b) 4-(3-Trimethylsilylphenylcarbamoyl)benzoic Acid

To a solution of 82 mg (0.25 mmol) of methyl 4-(3-trimethyl-silylphenylcarbamoyl)benzoate in 2 ml of EtOH was added 1 ml (2 mmol) of 2N sodium hydroxide solution and the mixture was stirred at room temperature for 4 hours. The reaction mixture was neutralized with 1N hydrochloric acid and extracted with AcOEt. The extract was washed sucessively with hydrochloric acid and sat.aq.NaCl, dried and evaporated. The residue was recrystallized from MeOH to give 48 mg of white prisms, m.p.211–213° C. (yield 61%).

MS spectrum m/z: 313(M$^+$), 298(M$^+$ –15), 149(0$^+$=C-C$_6$H$_4$—COOH).

IR spectrum vcm$^{-1}$: 1694, 1669.

$^1$H-NMR spectrum δ(CDCl$_3$-DMSO-d$_6$)ppm: 0.29 (9H,s), 7.3–7.8 (4H,m), 8.05 (2H,d,J=8 Hz), 8.13 (2H,d,J=8 Hz), 9.66 (1H,br).

High resolution mass spectrum for C$_{17}$H$_{19}$NO$_3$Si: Calculated m/z: 313.1133. Found m/z: 313.1164.

REFERENCE 3

3,5-Bis(trimethylsilyl)aniline a) 1-Nitro-3,5-bis(trimethylsilyl)benzene

To a solution of 1.18 g (4.00 mmol) of sym-tris(trimethylsilyl)benzene in 1.7 ml of acetic anhydride was added a solution of 0.4 ml (9.1 mmol) of 94% nitric acid in 1.7 ml of acetic anhydride at −10° C. The mixture was stirred at 10 to −5° C. for 2 hours and then at room temperature for 22 hours. The reaction mixture was poured into sodium hydroxide solution and the aqueous solution was extracted with methylene chloride. The extract was evaporated. The residue was purified by column chromatography on silica gel [eluent: petroleum ether] to give 636 mg of pale yellow crystals, m.p.86°–87° C. (yield 59%).

$^1$H-NMR spectrum δ(CDCl$_3$)ppm: 0.33 (18H,s), 7.90 (1H,t,J=1.1 Hz), 8.29 (2H,d,J=1.1 Hz).

b) 3,5-Bis(trimethylsilyl)aniline

1-Nitro-3,5-bis(trimethylsilyl)benzene (264 mg, 0.99 mmol) was catalytically hydrogenated over 10% Pd-C in 15 ml of benzene at atmospheric pressure for 135 minutes. The catalyst was filtered off and washed with benzene. The filtrate and washings were mixed and evaporated. The residue was purified by column chromatography on silica gel [eluent: methylene chloride-n-hexane (2:1)] to give 224 mg of light tan-colored low melting solid (yield 96%).

$^1$H-NMR spectrum δ(CDCl )ppm: 0.24 (18H,s), 3.36 (2H,brs), 6.84 (2H,brs), 7.07 (1H,brs).

EXAMPLE 2

4-(3,5-Trimethylsilylphenylcarbamoyl)benzoic Acid a) Methyl 4-(3,5-Trimethylsilylphenylcarbamoyl)-benzoate To a solution of 220 mg (0.93 mmol) of 3,5-bis(trimethylsilyl)aniline and 187 mg (0.94 mmol) of methyl p-chloroformylbenzoate in 10 ml of dry benzene was added 1 ml of dry pyridine. The mixture was stirred for 5.75 hours. Water was added to the reaction mixture and the aqueous layer was extracted with AcOEt. The extract was washed with 0.2M aqueous copper nitrate solution, water and sat.aq.NaHCO$_3$, successively, dried and evaporated. The residue was recrystallized from a mixture of methylene chloride and n-hexane to give 352 mg of white prisms, m.p.212.5°–213.5° C. (yield 95%).

$^1$H-NMR spectrum δ(CDCl$_3$)ppm: 0.30 (18H,s), 3.97 (3H,s), 7.46 (1H,t,J=1.1 Hz), 7.76 (2H,d,J=1.1 Hz), 7.79 (1H,brs), 7.96 (2H,d,J=8.4 Hz), 8.17 (2H,d,J=8.4 Hz).

b) 4-(3,5-Trimethylsilylphenylcarbamoyl)benzoic Acid

To a solution of 300 mg (0.75 mmol) of methyl 4-(3,5-trimethylsilylphenylcarbamoyl)benzoate in 5 ml of EtOH was added 3 ml of 2N sodium hydroxide solution and the mixture was stirred at room temperature overnight. The pH of the reaction mixture was adjusted to 3.0 with 2N hydrochloric acid. The aqueous solution was extracted with AcOEt. The extract was dried and evaporated. The white residue was recrystalized from a mixture of AcOEt and cyclohexane and washed with n-hexane to give 255 mg of white needles, m.p. 252°–253.5° C. (yield 88%).

$^1$H-NMR spectrum $\delta$(CDCl$_3$)ppm: 0.30 (18H,s), 7.46 (1H,t,J=1.1 Hz), 7.77 (2H,brs), 7.80 (1H,brs), 7.99 (2H,d,J=8.1 Hz), 8.21 (2H,d,J=8.1 Hz)

High resolution mass spectrum for C$_{20}$H$_{27}$NO$_3$Si$_2$: Calculated m/z : 385.1528. Found m/z : 385.1505.

REFERENCE 4

3,5-Bis(trimethylsilyl)benzoic Acid

A suspension of 2.0 g (14 mmol) of Ca(OCl)$_2$, 1.38 g(10 mmol) of potassium carbonate and 0.40 g (7.12 mmol) of potassium hydroxide in 40 ml of water was stirred at 65° C. for 30 minutes and filtered. The filtrate was added to 0.53 g (2 mmol) of 3′,5′-bis(trimethylsilyl)acetophenone and the mixture was refluxed for 7.5 hours with stirring. After cooling, 3 ml of aqueous sodium bisulfite solution was added to the reaction mixture. The aqueous solution was extracted with AcOEt. The extract was washed successively with water and sat.aq.NaCl, dried over anhyd.Na$_2$SO$_4$ and evaporated. The residue was purified by column chromatography on silica gel [eluent: n-hexane-AcOEt (2:1–1:1)] to give 0.27 g of white powder, m.p.>300° C. (yield 51%).

MS spectrum m/z: 266 (M+).

$^1$H-NMR spectrum $\delta$(CDCl$_3$)ppm: 0.32 (18H,s), 7.88 (1H,t,J=1.1 Hz), 8.24 (2H,d,J=1.1 Hz).

EXAMPLE 3

4-[3,5-Bis(trimethylsilyl)phenylcarboxamido]benzoic Acid a) Methyl 4-[3,5-Bis(trimethylsilyl)phenylcarboxamido]benzoate To a suspension of 1.064 g (4 mmol) of 3,5-bis(trimethylsilyl)benzoic acid and 1.05 g of potassium carbonate in 104 ml of dry benzene were added 0.64 ml (8.8 mmol) of thionyl chloride and 0.34 ml (4.4 mmol) of N,N-dimethylformamide (DMF) at room temperature with stirring. The mixture was stirred at room temperature for 3 hours and the insoluble substance was filtered off. The filtrate was evaporated and the residue was dissolved in 25 ml of dry tetrahydrofuran. To the solution were added 1.23 ml (8.8 mmol) of triethylamine and 0.665 g (4.4 mmol) of methyl p-aminobenzoate and the mixture was stirred at room temperature overnight. The reaction mixture was made weakly acid with 0.5N hydrochloric acid and extracted with methylene chloride. The extract was successively washed with water and sat.aq.NaCl, dried over anhyd.Na$_2$SO$_4$ and evaporated. The residue was purified by column chromatography on silica gel (eluent: n-hexane-AcOEt (5:1)) to give 1.34 g of pale yellow crystals, m.p.191°–192° C. (yield 84%).

MS spectrum m/z: 399 (M+)

$^1$H-NMR spectrum $\delta$(CDCl$_3$) ppm: 0.31 (18H,s), 3.90 (3H,s), 7.74 (2H,d,J=8.8 Hz), 7.83 (1 H,t,J=1.1 Hz), 7.96 (2H,d,J=1.1 Hz), 8.04 (2H,d,J=8.8 Hz), 8.14 (1H, br.s).

b) 4-[3,5-Bis(trimethylsilyl)phenylcarboxamido]benzoic Acid

To a solution of 22 mg(0.055 mmol) of methyl 4-[3,5-bis(trimethylsilyl)phenylcarboxamido]benzoate in 6 ml of EtOH was added 3 ml of 2N aqueous sodium hydroxide solution and the mixture was stirred at room temperature overnight. The reaction mixture was made weakly acid with hydrochloric acid and extracted with AcOEt. The extract was washed with sat.aq.NaCl, dried over MgSO$_4$ and evaporated. The residue was recrystallized from a mixture of AcOEt and n-hexane to give 14 mg of colorless prisms, m.p.276°–280° C. (dec.) (yield 66%).

MS spectrum m/z : 385 (M+)

$^1$H-NMR spectrum $\delta$(CDCl$_3$) ppm: 0.33 (18H,s), 7.78 (2H,d,J=8.8 Hz), 7.84 (1H,br.s), 7.94 (2H,d,J=0.9 Hz), 8.14 (2H,d,J=8.8 Hz).

EXAMPLE 4

Methyl 4-[3,5-Bis(trimethylsilyl)phenylcarboxy]benzoate

To a suspension of 665 mg (2.5 mmol) of 3,5-bis(trimethylsilyl)bonzoic acid and 670 mg of potassium carbonate in dry benzene were added 0.40 ml (5.5 mmol) of thionyl chloride and 0.21 ml (2.75 mmol) of N,N-dimethylformamide at room temperature with stirring. The mixture was stirred at room temperature for 3 hours. The insoluble matter was filtered off and the filtrate was evaporated. The residue was dissolved in 17.5 ml of dry tetrahydrofuran and 0.77 ml(5.5 mmol), of triethylamine and 418 mg (2.75 mmol) of methyl p-hydroxybenzoate were added to the solution. The mixture was stirred at room temperature for 1 day. The reaction mixture was made weakly acid with hydrochloric acid and extracted with methylene chloride. The extract was successively washed with water and sat.aq.NaCl, dried over anhyd.Na$_2$SO$_4$ and evaporated.

The residue was purified by column chromatography on silica gel [eluent:n-hexane-AcOEt (10:1)] to give 930 mg of white crystals (yield 93%), which was recrystalized from an aqueous methanol to give 790 mg of colorless needles, m.p. 81°–82° C. (yield 79%).

MS spectrum m/z : 400(M+), 385(M+−15)

$^1$H-NMR spectrum $\delta$(CDCl$_3$) ppm:0.33 (18H,s), 3.93 (3H,s), 7.30 (2H,d,J=8.8 Hz), 7.91 (1H,t,J=0.9 Hz), 8.13 (2H,d,J=8.8 Hz), 8.30 (1H,d,J=0.9 Hz).

EXAMPLE 5

4-[(3-Trimethylsilylphenyl)ethenyl]benzoic Acid a) (m-Trimethylsilylbenzyl)phosphonium Bromide A solution of 730 mg (3.00 mmol) of m-trimethylsilylbenzyl bromide and 1.18 g (4.50 mmol) of triphenylphosphine in 10 ml of dry toluene was refluxed for 4.5hours in an atmosphere of argon (125°–135° C. by oil bath). The precipitate was collected by filtration, and washed with toluene to give 1.361 g of white crystals, which were dried in vacuo (yield 90%).

$^1$H-NMR spectrum $\delta$(CD3OD)ppm: 0.30 (9H,S), 5.13 (2H,d,J=16 Hz), 7.1–8.1 (19H,m).

b) Methyl 4-[(3-Trimethylsilylphenyl)ethenyl]benzoate (m-Trimethylsilylbenzyl)phosphonium bromide (758 mg, 1.50 mmol) and methyl 4-formylbenzoate (258 mg, 1.57 mmol) were added to a NaOMe-methanol solution, which was prepared from 40 mg (1.74 mmol) of Na metal and 15 ml of dry methanol, and the mixture was stirred for 17 hours. The precipitate (trans form) was collected by filtration, washed with a cooled mixture of MeOH and n-hexane, and dried in vacuo to give 115 mg of white crystals. The mother liquors were evaporated and dissolved in $CH_2Cl_2$. The insoluble substance was filtered off and the filtrate was evaporated. The residue was purified by column chromatography to give 60 mg of colorless oil (cis form, yield 13%), 158 mg of white crystals (trans form, total yield 59%) and 110 mg of interfraction (yield 23%).

The trans form was recrystallized from a mixture of $CH_2Cl_2$ and n-hexane to give 149 mg of white needles. The mother liquors were evaporated. The residue was recrystallized from n-hexane to give 120 mg of white needles (total 269 mg, yield 58%).

m.p.113°–114.5° C.

$^1$H-NMR spectrum $\delta$(CDCl )ppm: 0.30 (9H,s), 3.92 (3H,m), 7.0–7.6 (8H,m), 8.02 (2H,d,J=8 Hz).

Mass spectrum m/z: 310 (M+), 295 (M+ −15).

IR spectrum $v cm^{-1}$: 1723, 1282, 1250.

UV spectrum $\lambda_{max}$ nm(log$\epsilon$): 323 (4.91), 232 (4.61), 209 (4.75).

The physical properties of the cis form were as follows.

$^1$H-NMR spectrum $\delta$(CDCl$_3$)ppm: 0.16 (9H,s), 3.90 (3H,s), 6.59 (1H,d,J=12 Hz), 6.69 (1H,d,J=12 Hz), 7.1–7.4 (6H,m), 7.87 (2H,d,J=8 Hz).

IR spectrum $v cm^{-1}$: 1724, 1280, 1250.

UV spectrum $\lambda_{max}$ nm(log$\epsilon$): 303 (3.97), 237 (4.19), 203 (4.24).

(c) 4-[(3-Trimethylsilylphenyl)ethenyl]benzoic Acid

A solution of 1.8 ml(3.6 mmol) of 2N-KOH was added to a solution of 143 mg (0.461 mmol) of trans-methyl 4-[(3-trimethylsilylphenyl)ethenyl]benzoate in 3 ml of EtOH. The mixture was stirred at room temperature. The reaction mixture was adjusted to acid pH with 2N hydrochloric acid, and then the aqueous solution was extracted with AcOEt. The extract was dried and evaporated to give 137 mg of the title compound as white crystals (yield 100%), which were recrystallized from a mixture of ethyl acetate, methylene chloride and n-hexane, and dried to give 116 mg of white crystals, m.p.216°–218° C. (yield 85%).

$^1$H-NMR spectrum $\delta$(CDCl$_3$-DMSO-d$_6$)ppm: 0.30 (9H,s), 7.12 (1H,d,J=18 Hz), 7.25 (1H,d,J=18 Hz), 7.4–7.8 (6H,m), 7.95 (2H,d,J=8 Hz).

IR spectrum $v cm^{-1}$: 1670.

High resolution mass spectrum for $C_{18}H_{20}O_2Si$: Calculated m/z: 296.1232. Found m/z: 296.1250.

EXAMPLE 6

4-[3-(3-Trimethylsilylphenyl)-3-oxo-1-propenyl]benzoic Acid

To a solution of 130 mg (0.676 mmol) of 3'-trimethylsilylacetophenone and 127 mg (0.774 mmol) of methyl 4-formylbenzoate in 4.5 ml of tetrahydrofuran(THF) were added 128 mg (3.20 mmol) of NaOH and 3 ml of hot water, and the mixture was stirred at room temperature overnight. The reaction mixture was adjusted with 7 ml of 0.5N-HCl to pH6, and then the aqueous solution was extracted with ethyl acetate. The extract was washed with 0.05N-HCl and $H_2O$, dried and evaporated. The residue was purified by column chromatography affording 133 mg of pale yellow powder (yield 61%), which was recrystallized from a mixture of methylene chloride, methanol and n-hexane to give 98 mg of pale yellow needles, m.p.179°–180° C. (yield 45%).

$^1$H-NMR spectrum $\delta$(CDCl$_3$)ppm1 : 0.33 (9H,s), 7.51 (1H,t,J=7.7 Hz), 7.62 (1H,d,J=15.8 Hz), 7.74 (2H,d,J=8.1 Hz), 7.76 (1H,d,J=7.7 Hz), 7.82 (1H,d,J=15.8 Hz), 7.99 (1H,d,J=7.7 Hz), 8.14 (2H,d,J=8.1 Hz), 8.15 (1H,m).

EXAMPLE 7

4-[3-(3,5-Bistrimethysilylphenyl)-3-oxo-1-propenyl]-benzoic Acid

Under ice-cooling, to a solution of 114 mg (0.43 mmol) of 3',5'-bis(trimethylsilyl)acetophenone and 70 mg (0.43 mmol) of methyl 4-formylbenzoate in 3 ml of THF was added a solution of 40 mg (1.00 mmol) of NaOH in 2 ml of $H_2O$ with stirring, and the mixture was stirred in an atmosphere of prepurified argon overnight. The reaction mixture was further added to 39 mg of NaOH, stirred for 2 days, and then the solution was adjusted with 2N-HCl to pH$\leq$7 and extracted with ethyl acetate. The extract was dried and evaporated. The residue was purified by column chromatography using methylene chloride-methanol (10:1) as an eluant to give 112 mg of the desired compound (yield 66%), which was recrystallized from a mixture of ethyl acetate and n-hexane to give 98 mg of pale yellow prisms, m.p.194°–195.5° C. (yield 57%).

$^1$H-NMR spectrum $\delta$(CDCl )ppm: 0.33 (18H,s), 7.59 (1H,d,J=15.7 Hz), 7.73 (2H,d,J=8.1 Hz), 7.80 (1H,d,J=15.7 Hz), 7.87 (1H,t,J=1.1 Hz), 8.10 (2H,d,J=1.1 Hz), 8.16 (2H,d,J=8.1 Hz), High resolution mass spectrum for $C_{22}H_{28}O_3Si_2$: Calculated m/z: 396.1575. Found m/z: 396.1558.

REFERENCE 5

3'-Trimethylgermylacetophenone a) 2-(3-Trimethylgermylphenyl)-2-methyl-1,3-dioxolane A mixture of 81 mg (3.33 mmol) of magnesium and 574 mg (3.75 mmol) of trimethylgermyl chloride was stirred at 40°–50° C. in an atmosphere of argon. To the mixture was added a solution of 729 mg (3.00 mmol) of 2-(3-bromophenyl)-2-methyl-1,3-dioxolane in 10 ml of tetrahydrofuran with stirring. The mixture was refluxed for 2.5hr. and stirred at room temperature overnight. To the reaction mixture was added petroleum ether and the insoluble substance was filtered off. The filtrate was evaporated to give 874 mg of pale yellow crystals, which were purified by column chromatography on silica gel [eluent: methylene chloride-n-hexane (1:1)] to give 657 mg of white cubes, m.p.62.5°–63.5° C. (yield 78%).

$^1$H-NMR spectrum $\delta$(CDCl )ppm: 0.39 (9H,s), 1.67 (3H,s), 3.75–3.83 (2H,m), 4.00–4.09 (2H,m), 7.33 (1H,t,J=7.4 Hz), 7.41 (1H,dt,J=7.4,1.3 Hz), 7.44 (1H,ddd,J=7.4,1.9,1.3 Hz), 7.58 (1H,m).

$^{13}$H-NMR spectrum $\delta$(CDCl$_3$)ppm: −1.76, 27.71, 64.42, 108.98, 125.24, 127.66, 129.50, 132.43, 142.53, 142.56 b) 3'-Trimethylgermylacetophenone

A mixture of 351 mg (1.25 mmol) of 2-(3-trimethylgermylphenyl)-2-methyl-1,3-dioxolane, 47 mg (0.187 mmol, 0.15eq) of pyridinium p-toluenesulfonate (PPTS), 1.1126 g (62.5 mmol, 50eq) of water and 10 ml of acetone was refluxed for 2.5hours. The reaction mixture was evaporated and extracted with petroleum ether. The extract was evaporated. The oily residue was purified by column chromatography to give 294 mg of colorless oily substance.

$^1$H-NMR spectrum $\delta$(CDCl$_3$)ppm: 0.42 (9H,s), 2.62 (3H,s), 7.44 (1H,ddd,J=7.7,7.3,0.6 Hz), 7.67

(1H,dt,J=7.3,1.3 Hz), 7.90 (1H,ddd,J=7.7,1.9,1.3 Hz), 8.06 (1H,ddd,J=1.9,1.3,0.6 Hz)

EXAMPLE 8

4-[3-(3-Trimethylgermylphenyl)-3-oxo-1-propenyl]benzoic Acid

3'-Trimethylgermylacetophenone (49 mg,0.2 mmol) and methyl 4-formylbenzoate (37 mg,0.23 mmol) was dissolved in 5 ml of a mixture of 50% isopropanol and tetrahydrofuran, 1 ml of 1N aqueous potassium hydroxide solution was added, and the mixture was stirred overnight. The reaction mixture was adjusted to pH1 with 2N hydrochloric acid and extracted with AcOEt. The extract was evaporated and the residue was purified by column chromatography on silica gel (eluent: MeOH-methylene chloride) and recrystallized from a mixture of AcOEt and n-hexane to give 17 mg of pale yellow prisms, m.p.186°-188° C. (yield 22%).

$^1$H-NMR spectrum $\delta$(CDCl$_3$)ppm: 0.45 (9H,s), 7.50 (1H,dd,J=7.9,7.3 Hz), 7.62 (1H,d,J=15.8 Hz), 7.72 (1H,dt,J=7.3,1.3 Hz), 7.74 (1H,d,J=8.4 Hz), 7.83 (1H,d,J=15.8 Hz),8.11 (1H,m), 8.14(1H,d,J=8.4 Hz).

REFERENCE 6

3'5'-Bis(trimethylgermyl)acetophenone a) 2-(3,5-Bis(trimethylgermyl)phenyl]-2-methyl-1,3-dioxolane and 2-(3-Trimethylgermyl)-2-methyl-1,3-dioxolane To a suspension of 108 mg (4.44 mmol) of magnesium and 765 mg (5.00 mmol) of trimethylgermyl chloride was added a solution of 644 mg (2.00mmol) of 2-(3,5-dibromophenyl)-2-methyl-1,3-dioxolane in 10 ml of tetrahydrofuran at 40° C., stirred in an atmosphere of argon. The mixture was stirred at 70° C. for 4.5hr. and at room temperature overnight. The reaction mixture was poured into ice-aqueous sodium bicarbonate solution and extracted with methylene chloride. The solvent was removed to give pale brown crystals, which were purified by column chromatography on silica gel [eluent: methylene chloride-n-hexane (1:1)] to give 514 mg (yield 65%) of 2-(3,5-bis(trimethylgermyl)phenyl]-2-methyl-1,3-dioxolane, m.p.54° C., and 61 mg (yield 11%) of 2-(3-trimethylgermylphenyl)-2-methyl-1,3-dioxolane and 75 mg of the mixture, in which the ratio was 3:2 (by NMR).

The physical properties of 2-(3,5-bis(trimethylgermyl)phenyl]-2-methyl-1,3-dioxolane were as follows:

$^1$H-NMR spectrum $\delta$(CDCl$_3$)ppm: 0.39 (18H,s), 1.68 (3H,s), 3.76-3.83 (2H,m), 4.01-4.10 (2H,m), 7.50 (1H,t,J=1.1 Hz), 7.55 (2H,d,J=1.1 Hz)

The physical properties of 2-(3-trimethylgermylphenyl)-2-methyl-1,3-dioxolane were as follows.

$^1$H-NMR spectrum $\delta$(CDCl$_3$)ppm: 0.39 (9H,s), 1.67 (3H,s), 3.75-3.84 (2H,m), 4.00-4.09 (2H,m), 7.33 (1H,t,J=7.3 Hz), 7.41 (1H,ddd,J=7.3,1.5,1.1 Hz), 7.44 (1H,ddd,J=7.3,1.8,1.5 Hz), 7.58 (1H,m).

b)3',5'-Bis(trimethylgermyl)acetophenone

A mixture of 240 mg (0.60 mmol) of 2-[3,5-bis(trimethylgermyl)phenyl]-2-methyl-1,3-dioxolane, 23 mg (0.090 mmol) of PPTS, 10.6 ml of acetone (excess) and 540 mg (30 mmol) of water was refluxed for 2.5hours. The reaction mixture was evaporated and extracted with ether. The extract was evaporated to give 208 mg of pale yellow crystals, which were sublimed at 70° C., 0.5mmHg to give 189 mg of white prisms, m.p.56° C. (yield 89%).

$^1$H-NMR spectrum $\delta$(CDCl$_3$)ppm: 0.43 (18H,s), 2.63 (3H,s), 7.74 (1H,t,J=1.1 Hz), 7.99 (2H,d,J=1.1 Hz). IR spectrum $\nu$cm$^{-1}$: 1986

EXAMPLE 9

4-[3-(3,5-Bistrimethylgermylphenyl)-3-oxo-1-propenyl]benzoic Acid

3',5'-Bis(trimethylgermyl)acetophenone 163 mg (0.46 mmol) and 96 mg (0.58 mmol) of methyl 4-formylbenzoate was dissolved in 4 ml of a mixture of isopropanol and tetrahydrofuran (1:1). To the mixture was added 2.5 ml of 0.75N aqueous potassium hydroxide solution with stirring and the mixture was stirred at room temperature overnight. The reaction mixture was adjusted to pH3.8 with 0.2N hydrochloric acid and extracted with AcOEt. The extract was evaporated. The residue was purified by column chromatography on silicagel [eluent: methylene chloride-MeOH (10:1)] and recrystallized from a mixture of methylene chloride, MeOH and n-hexane to give 120 mg of yellow prisms, m.p.194°-195.5° C. (dec.).

$^1$H-NMR spectrum $\delta$(CDCl$_3$)ppm: 0.45 (18H,s), 7.59 (1H,d,J=15.8 Hz), 7.74 (2H,d,J=8.3 Hz), 7.78 (1H,t,J=1.1 Hz), 7.81 (1H,d,J=15.8 Hz), 8.03 (2H,d,J=1.1 Hz),8.16 (2H,d,J=8.3 Hz).

Analysis for C$_{22}$H$_{28}$O$_3$Ge$_2$: Calculated: C,54.41; H,5.81; N,0. Found: C,54.57; H,5.94; N,0.

REFERENCE 7

2'-Hydroxy-5'-trimethylsilylacetophenone a) 2-(2-Trimethylsilyloxy-5-bromophenyl)-2-methyl-1,3-dioxolane Under ice-cooling, to a solution of 3.11 g (12 mmol) of 2-(2-hydroxy-5-bromophenyl)-2-methyl-1,3-dioxolane in 24 ml of tetrahydrofuran was added dropwise succesively, 1.84 ml (13.2 mmol) of triethylamine and 1.68 ml (13.2 mmol) of trimethylsilyl chloride with stirring. The mixture was stirred at room temperature for 2 hours and filtered. The filtrate was concentrated under reduced pressure to give 4.0 g of the crude product.

b) 2'-Hydroxy-5'-trimethylsilylacetophenone

A mixture of 321 mg (13.2 mmol) of magnesium, 0.07 ml of ethyl iodide and 1.32 ml of dry tetrahydrofuran was refluxed. After cooling, the mixture was diluted with 3.96 ml of dry tetrahydrofuran and refluxed. To the mixture was added dropwise a solution 4.0 g of crude 2-(2-trimethylsilyloxy-5-bromophenyl)-2-methyl-1,3-dioxolane, obtained as above, in 9.6 ml of tetrahydrofuran and the reaction mixture was refluxed for 2 hours. After cooling, 1.68 ml (13.2 mmol) of trimethylsilyl chloride was added and refluxed for 3 hours. Water was added to the reaction mixture. The mixture was extracted with ether. The extract was washed with water and sat.aq.NaCl, dried over anhyd.Na$_2$SO$_4$ and evaporated. To the residue was added 72 ml of acetone, 10.8 ml (600 mmol) of water and 0.46 g (1.8 mmol) of PPTS. The mixture was refluxed for 3 hours and evaporated. The residue was dissolved in ether. The solution was washed with water, aqueous sodium bicarbonate solution and sat.aq.NaCl, dried over anhyd.Na$_2$SO$_4$ and evaporated. The residue was purified by column chromatography on silica gel [eluent: n-hexane-AcOEt (20:1)] to 1.66 g of pale yellow liquid (yield 67%).

MS spectrum m/z: 208(M$^+$), 193(M$^+$−15).

¹H-NMR spectrum δ(CDCl₃)ppm: 0.28 (9H,s), 2.65 (3H,s), 6.96 (1H,d,J=7.9 Hz), 7.59 (1H,dd,J=7.9,1.8 Hz), 7.84 (1H,d,J=1.8 Hz) 12.31 (1H,s).

EXAMPLE 10

4-[1-Hydroxy-3-(2-hydroxy-5-trimethylsilylphenyl)-3-oxo-1propenyl]benzoic Acid a) 2-Acetyl-4-trimethylsilylphenyl Methyl 1,4-Benzenedicarboxylate Under ice-cooling, to a solution of 832 mg (4 mmol) of 2'-hydroxy-5'-timethylsilylacetophenone in 20 ml of tetrahydrofuran were added dropwise successively, 0.61 ml (4.4 mmol) of triethylamine and 874 mg (4.4 mmol) of methyl p-chloroformylbenzoate with stirring. The mixture was stirred at room temperature for 1 day and filtered. The filtrate was evaporated and the residue was dissolved in AcOEt. The organic solution was washed with H₂O, aqueous sodium bicarbonate solution and brine, dried over anhydrous Na₂SO₄ and evaporated. The residue was purified by column chromatography on silica gel [eluent: n-hexane-AcOEt (5:1)] to give 1.25 g of white crystals (yield 85%), m.p.88.5–90.5° C..

MS spectrum m/z: 370 (M+).

¹H-NMR spectrum δ(CDCl₃)ppm: 0.32 (9H,s), 2.55 (3H,s), 3.97 (3H,s), 7.22 (1H,d,J=7.7 Hz), 7.73 (1H,dd,J=7.7,1.5 Hz), 7.97 (1H,d,J=1.5 Hz), 8.16 (2H,d,J=8.8 Hz), 8.29 (2H,d,J=8.8 Hz).

b) Methyl 4-[1-Hydroxy-3-(2-hydroxy-5-trimethylsilylphenyl)-3-oxo-1-propenyl]benzoate To a solution of 740 mg (2 mmol) of 2-acetyl-4-trimethylsilylphenyl methyl 1,4-benzenedicarboxylate in 14 ml of pyridine was added 280 mg (5 mmol) of ground potassium hydroxide at room temperature with stirrig. The mixture was stirred at room temperatre overnight and poured into a chilled 20%-aqueous solution of acetic acid. A deposited precipitation was extracted with AcOEt. The extract was washed with H₂O and saturated aq.NaCl, dried over Na₂SO₄ and evaporated. The residue was purified by column chromatography on silica gel [eluent: n-hexane-AcOEt (5:1)] to give 200 mg of yellow crystals (yield 27%), m.p.129.5°–131° C.

MS spectrum m/z: 370 (M+).

¹H-NMR spectrum δ(CDCl₃)ppm: 0.31 (9H,s), 3.96 (3H,s), 6.88 (1H,s), 7.00 (1H,d,J=7.9 Hz), 7.61 (1H,dd,J=7.9,1.3 Hz), 7.85 (1H,d,J=1.3 Hz), 7.97 (2H,d,J=8.8 Hz), 8.17 (2H,d,J=8.8 Hz), 12.04 (1H,s), 15.44 (1H,s).

c) 4-[1-Hydroxy-3-(2-hydroxy-5-trimethylsilylphenyl)-3-oxo-1propenyl]benzoic Acid To a solution of 148 mg (0.4 mmol) of methyl 4-[1-hydroxy-3(2-hydroxy-5-trimethylsilylphenyl)-3-oxo-1-propenyl] benzoate in 20 ml of ethanol was added 2 ml of 2N-sodium hydroxide solution at room temperature with stirring. The mixture was stirred at room temperature for 1 day and acidified with 10%-hydrochloric acid to pH 4. A deposited precipilation was extracted with AcOEt. The extract was washed with H₂O and saturated aq.NaCl, dried over MgSO₄, and evaporated. The residue was recrystallized from methanol to give 72 mg of yellow needles (yield 51%), m.p.207°–209° C.

MS spectrum m/z: 356 (M+).

¹H-NMR spectrum δ(DMSO-d₆)ppm: 0.26 (9H,s), 6.84–8.30 (8H,m).

REFERENCE 8

2'-Hydroxy-4'-trimethylsilylacetophenone a) 2-(4-Bromo-2-trimethylsilyloxyphenyl)-2-methyl-1,3-dioxolane Under ice-cooling, to a solutin of 3.11 g (12 mmol) of 2-(2-hydroxy-4-bromophenyl)-2-methyl-1,3-dioxolane in 24 ml of tetrahydrofuran were added dropwise successively, 1.84 ml (13.2 mmol) of triethylamine and 1.68 ml (13.2 mmol) of trimethylsilyl chloride with stirring. The mixture was stirred at room temperature for 3 hours and filtered. The filtrate was concentrated under reduced pressure to give 4.0 g of the crude product.

b) 2'-Hydroxy-4'-trimethylsilylacetophenone

A mixture of 321 mg (13.2 mmol) of magnesium and 0.07 ml of methyl iodide in 1.32 ml of dry tetrahydrofuran was refluxed. After cooling, the mixture was diluted with 3.96 ml of dry tetrahydrofuran. To the mixture was added a solution of 4.0 g of crude 2-(4-bomo-2-trimethylsilyloxyphenyl)-2-methyl-1,3-dioxolane obtained above in 9.6 ml of dry tetrahydrofuran dropwise under refluxing and the mixture was refluxed for additional 2 hours. After cooling, 1.68 ml (13.2 mmol) of trimethylsilyl chloride was added to the reaction mixture and the mixture was refluxed for 2 hours. After cooling, water was added to the reaction mixture. The mixture was extracted with ether. The organic layer was washed with H₂O and brine, dried over anhydrous Na₂SO₄, and evaporated. To the residue were added 72 ml of acetone, 10.8 ml (600 mmol) of water and 0.46 g (1.8 mmol) of pyridinium p-toluenesulfonate (PPTS). The mixture was refluxed for 4 hours, neutralized with aqueous sodium bicarbonate solution, and evaporated. The residue was dissolved in ether. The solution was washed with water, sodium bicarbonate and brine, dried over anhydrous Na₂SO₄, and evaporated. The residue was purified by column chromatography on silica gel [eluent: n-hexane-AcOEt (15:1)] to give 1.08 g of pale yellow liquid (yield 43%).

MS spectrum m/z: 208 (M+), 198 (M+ −15).

¹H-NMR spectrum δ(CDCl₃)ppm: 0.27 (9H,s), 2.63 (3H,s), 7.03 (1H,dd,J=7.9,1.3 Hz), 7.14 (1H,d,J=1.3 Hz), 7.69 (1H,d,J=7.9 Hz), 12.15 (1H,s).

EXAMPLE 11

4-[1-Hydroxy-3-(2-hydroxy-4-trimethylsilylphenyl)-3-oxo-1propenyl]benzoic Acid a) 2-Acetyl-5-trimethylsilylphenyl Methyl 1,4-Benzenedicarboxylate Under ice-cooling, to a solution of 832 mg (4 mmol) of 2'-hydroxy-4'-timethylsilylacetophenone in 20 ml of tetrahydrofuran were added dropwise successively, 0.61 ml (4.4 mmol) of triethylamine and 874 mg (4.4 mmol) of methyl p-chloroformylbenzoate with stirring. The mixture was stirred at room temperature for 1 day and filtered. The filtrate was evaporated and the residue was dissolved in AcOEt. The organic solution was washed with H₂O aqueous sodium bicarbonate solution and brine, dried over anhydrous Na₂SO₄ and evaporated. The residue was purified by column chromatography on silica gel eluent: n-hexane-AcOEt (5:1)] to give 1.40 g of pale yellow viscous liquid (yield 95%).

MS spectrum m/z: 370 (M+).

¹H-NMR spectrum δ(CDCl₃)ppm: 0.31 (9H,s), 2.54 (3H,s), 3.98 (3H,s), 7.34 (1H,d,J=1.1 Hz), 7.51 (1H,dd,J=7.5,1.1 Hz), 7.84 (1H,d,J=7.5 Hz), 8.16 (2H,d,J=9.0 Hz), 8.30 (2H,d,J=9.0 Hz).

b) Methyl 4-[1-Hydroxy-3-(2-hydroxy-5-trimethylsilylphenyl)-3-oxo-1-propenyl]benzoate To a solution of 740 mg (2 mmol) of 2-acetyl-4-trimethylsilylphenyl methyl 1,4-benzenedicarboxylate in 14 ml of pyridine was added 280 mg (5 mmol) of ground potassium hydroxide with stirring under ice-cooling. The mixture was stirred at same temperature for 1.5 hours and poured into a chilled 20%-aqueous solution of acetic acid. A deposited precipitation was extracted with AcOEt. The extract was washed with H$_2$O and brine, dried over anhydrous Na$_2$SO$_4$ and evaporated. The residue was purified by column chromatography on silica gel [eluent: n-hexane-AcOEt (5:1)] to give 510 mg of yellow crystals (yield 69%), m.p.152°–154° C.

MS spectrum m/z: 370 (M+).

$^1$H-NMR spectrum δ(CDCl$_3$)ppm: 0.29 (9H,s), 3.96 (3H,s), 6.89 (1H,s), 7.06 (1H,dd,J=7.9,0.9 Hz), 7.17 (1H,d,J=0.9 Hz), 7.73 (1H,d,J=7.9 Hz), 7.97 (2H,d,J=8.8 Hz), 8.15 (2H,d,J=8.8 Hz), 11.91 (1H,s), 15.41 (1H,s).

c) 4-[1-Hydroxy-3-(2-hydroxy-4-trimethylsilylphenyl)-3-oxo-1propenyl]benzoic Acid To a solution of 370 mg (1 mmol) of methyl 4-[1-hydroxy-3-(2-hydroxy-5-trimethylsilylphenyl)-3-oxo-1-propenyl]benzoate in 60 ml of ethanol was added 5 ml of 2N sodium hydroxide solution at room temperature with stirring. The mixture was stirred at room temperature overnight, neutralized with 10% hydrochloric acid to pH 8, and evaporated H$_2$O was added to the residue and the mixture was acidified with 10%-hydrochloric acid to pH4. A deposited precipitation was collected by filtration, dried, and recrystalized from N,N-dimethylformamide and ethanol to give 175 mg of yellow plates (yield 49%), m.p. 288°–291° C. (decomp.).

MS spectrum m/z: 356 (M+).

$^1$H-NMR spectrum δ(DMSO-d$_6$)ppm: 0.27 (9H,s), 7.00–8.24 (8H,m).

It is to be understood that the invention is not to be limited to the exact details of operation, or to the exact compositions, methods, procedures, or embodiments shown and described, as modifications and equivalents will be apparent to one skilled in the art, and the invention is therefore to be limited only by the full scope of the appended claims.

What is claimed is:

1. A benzoic acid derivative represented by the formula (I)

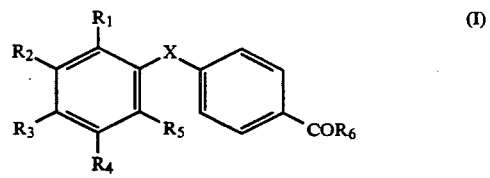

wherein R$_1$ represents hydrogen or lower-alkyl, R$_2$ and R$_4$ represent hydrogen, or trimethylgermyl, R$_3$ represents hydrogen, lower-alkyl, or trimethylgermyl, R$_5$ represents hydrogen, lower-alkyl, acetyl or hydroxy, at least one of R$_2$ and R$_3$ being trimethylgermyl, and R$_6$ means hydroxy, lower-alkoxy, or a group of the formula —NR$_7$R$_8$, wherein R$_7$ and R$_8$ mean hydrogen or lower-alkyl, and X represents a group of the formula —NHCO— or —COCH=CH—.

2. A compound of claim 1 which is 4-[3-[3,5-Bis(-trimethylgermyl) phenyl]-3-oxo-1-propenyl]benzoic acid.

3. A compound of claim 1 which is 4-[3-(3-trimethylgermylphenyl)-3-oxo-1-propenyl]benzoic acid.

4. A therapeutic agent useful for treatment of psoriasis comprising as active ingredient an effective amount of a compound as claimed in claim 1, 2, or 3, together with a pharmaceutically-acceptable diluent or carrier.

5. A therapeutic agent useful for treatment of immune and inflammatory diseases comprising as active ingredient an effective amount of a compound as claimed in claim 1, 2, or 3, together with a pharmaceutically-acceptable diluent or carrier.

6. A method of differentiating neoplastic cells comprising the step of employing as the active differentiation-inducing reagent an amount of a compound as claimed in claim 1, 2, or 3, which is effective for such purpose.

7. The method of claim 6, wherein the neoplastic cells are leukemia cells.

* * * * *

UNITED STATES PATENT AND TRADEMARK OFFICE
CERTIFICATE OF CORRECTION

PATENT NO. : 5,081,271

DATED : Jan. 14, 1992

INVENTOR(S) : Koichi Shudo

It is certified that error appears in the above-identified patent and that said Letters Patent is hereby corrected as shown below:

```
Title Page [56],  Attorney, Agent, or Firm;    "Gordon W. Kueschen"
   should read -- Gordon W. Hueschen --.
Title Page [57] ABSTRACT, 10th line after the formula; "—COHN—"
   should read -- —CONH— --.
Column 2, line 66; "derivatives" should read -- derivative --.
Column 8, line 35; "is" should read -- are --.
Column 8, approximately line 46; begin a new paragraph with "To".
Column 9, line 54/55; "chlomatography" should read --chromatography--.
Column 9, line 61; "(CDCl )" should read -- (CDCl$_3$) --.
Column 10, line 44; "(CDCl )" should read -- (CDCl$_3$) --.
Column 12, line 58; "(CD3OD)" should read -- (CD$_3$OD) --.
Column 13, line 66; "ppml:" should read -- ppm: --.
Column 14, line 24; "(CDCl)" should read -- (CDCl$_3$) --.
Column 14, line 50; "(CDCl)" should read -- (CDCl$_3$) --.
Column 17, approximately line 7; "oxo-1propenyl" should read
   -- oxo-1-propenyl --.
Column 17, line 36; "stirrig." should read -- stirring. --.
```

UNITED STATES PATENT AND TRADEMARK OFFICE
CERTIFICATE OF CORRECTION

PATENT NO. : 5,081,271
DATED : Jan. 14, 1992
INVENTOR(S) : Koichi Shudo

It is certified that error appears in the above-identified patent and that said Letters Patent is hereby corrected as shown below:

Column 17, line 37; "temperatre" should read -- temperature --.
Column 17, line 53; "1propenyl" should read -- 1-propenyl --.
Column 17, approximately line 61; "precipilation" should read -- precipitation --.
Column 18, approximately line 47; "oxo-1propenyl" should read -- oxo-1-propenyl --.
Column 18, line 52; "timethylsilylacetophenone" should read -- trimethylsilylacetophenone --.
Column 18, line 62; "eluent:" should read -- [eluent: --.
Column 19, line 23; "1propenyl" should read -- 1-propenyl --.

Signed and Sealed this

Eighth Day of June, 1993

Attest:

MICHAEL K. KIRK

*Attesting Officer*  Acting Commissioner of Patents and Trademarks